(12) United States Patent
Hsieh et al.

(10) Patent No.: US 7,297,500 B2
(45) Date of Patent: Nov. 20, 2007

(54) USE OF TROPONIN I AS A SPECIES MARKER PROTEIN FOR MEAT SPECIATION IN BOTH RAW AND HEAT-PROCESSED PRODUCTS

(75) Inventors: Yun-Hwa Peggy Hsieh, Auburn, AL (US); Fur-Chi Chen, Montgomery, AL (US)

(73) Assignee: Auburn University, Auburn University, AL (US)

( * ) Notice: Subject to any disclaimer, the term of this patent is extended or adjusted under 35 U.S.C. 154(b) by 374 days.

(21) Appl. No.: 10/077,020

(22) Filed: Feb. 15, 2002

(65) Prior Publication Data

US 2003/0022248 A1    Jan. 30, 2003

Related U.S. Application Data (60) Provisional application No. 60/286,045, filed on Apr. 23, 2001, provisional application No. 60/269,055, filed on Feb. 15, 2001.

(51) Int. Cl.
*G01N 33/53* (2006.01)

(52) U.S. Cl. .................. 435/7.1; 435/1.1; 435/7.2; 435/40.52; 435/284.1; 435/287.2; 436/63; 436/517; 436/548

(58) Field of Classification Search .............. 435/2, 435/6, 7.2, 7.21, 7.92–7.95, 288.3, 971, 1.1, 435/7.1, 284.1, 287.2; 436/513, 63, 514, 436/515, 518, 523, 524, 528, 548, 517
See application file for complete search history.

(56) References Cited

U.S. PATENT DOCUMENTS

| | | | |
|---|---|---|---|
| 6,288,215 B1 | 9/2001 | Hsieh | |
| 6,692,930 B2 * | 2/2004 | Hsieh | 435/7.92 |
| 2003/0040024 A1 * | 2/2003 | Katrukha et al. | 435/7.21 |

FOREIGN PATENT DOCUMENTS

WO    WO 98/08371 A1    3/1998

OTHER PUBLICATIONS

Hsieh et al., Monoclonal Antibodies against Heat-treated Muscle Proteins for Species Identification and End-Point Temperature Determination of Cooked Meats, Quality Attributes of Muscle Foods, pp. 287-307 (1999).*
Morales et al., Monoclonal Antibody Detection of Porcine Meat, Journal of Food Protection, 57 (2): 146-149 (Feb. 1994).*
Saisekhar et al. Use of Troponin for Species Udentification of Cattle and Buffalo Meats, J. Food Sci. Technol. 32 (1): 68-70 (1995).*
Haider et al., Production and characterisation of anti-cardiac troponin-I monoclonal antibodies, Disease markers, (Aug. 1995) vol. 12, No. 3, pp. 187-197).*

(Continued)

*Primary Examiner*—Gailene Rio-Gabel
(74) *Attorney, Agent, or Firm*—Alston & Bird LLP (57) ABSTRACT

Monoclonal antibodies are provided which bind to heat-treated proteins of meats. The antibodies are useful in detecting the presence of an exogenous meat in a cooked or raw meat sample. Furthermore, the antibodies can be used to determine the end point temperature of a meat sample.

9 Claims, 4 Drawing Sheets

Indirect ELISA test on reactivity of three TnI-MAbs to different species of meats heat-treated at 132 C for 2 h P=pork; B=beef; L=lamb; H=horse; De=deer; C=chicken:
T=turkey; Dk=duck; G=geese; O=ostrich

OTHER PUBLICATIONS

Chen, F. et al., "Troponin I as a Species Marker for Identification of Cooked Meats," International Congress on Authenticity of Species in Meat and Seafood Products, Sep. 18-20, 2000, Vigo, Spain, Oral Presentation.

Chen, F.-C. et al., "Monoclonal Antibodies to Porcine Thermal-Stable Muscle Protein for Detection of Pork in Raw and Cooked Meats," *Journal of Food Science*, 1998, pp. 201-205, vol. 63, No. 2.

Chen, F.-C. et al., "Separation and Characterization of a Porcine-specific Thermostable Muscle Protein from Cooked Pork," *Journal of Food Science*, 2001, pp. 799-803, vol. 66, No. 6.

Hseih, Y-H. P., et al., "Monoclonal Antibodies Against Heat-Treated Muscle Proteins for Species Identification and End-Point Temperature Determination of Cooked Meats," *Quality Attributes of Muscle Foods*, 1999, pp. 287-307, Kluwer Academic/Plenum Publishers, New York.

Morales, P. et al., "Monoclonal Antibody Detection of Porcine Meat," *Journal of Food Protection*, Feb. 1994, pp. 146-149, vol. 57, No. 2.

Chen, F-C, and Hsieh, Y-H P., Porcine Troponin I: A Thermostable Species Marker Protein, *Meat Science*, May 2002, pp. 55-60, vol. 61, No. 1.

Patterson, R.M., et al., "Improved Species Identification of Raw Meat by Double Sandwich Enzyme-linked Immunosorbent Assay," *J. Sci. Food Agric.*, 1994, pp. 1018-1023, vol. 35, No. 9.

Saisekhar, Y. and Reddy, P.M., "Use of Troponin for Species Identification of Cattle and Buffalo Meats," *J. Food Sci. Technol.*, 1995, pp. 68-70, vol. 32, No. 1.

\* cited by examiner

P=pork; B=beef; L=lamb; H=horse; De=deer; C=chicken; T=turkey; Dk=duck; G=geese; O=ostrich

FIG 4

USE OF TROPONIN I AS A SPECIES MARKER PROTEIN FOR MEAT SPECIATION IN BOTH RAW AND HEAT-PROCESSED PRODUCTS

CROSS-REFERENCE TO RELATED APPLICATIONS

This application claims the benefit of U.S. Provisional Application No. 60/286,045, filed Apr. 23, 2001, and U.S. Provisional Application No. 60/269,055, filed Feb. 15, 2001.

FEDERALLY SPONSORED RESEARCH OR DEVELOPMENT

This invention was made under contract with the USDA-NRI agency of the United States Government under Contract No. CSREES 99-35503-8135.

FIELD OF THE INVENTION

The present invention relates to the development of monoclonal antibodies for the detection of meat species, either raw or cooked meats, utilizing Troponin I as a speciation marker. Also provided are monoclonal antibodies specific to Troponin I.

BACKGROUND OF THE INVENTION

The accurate labeling of meat products is mandated and monitored by the United States Department of Agriculture (USDA) as well as by state and local governments. Mixing undeclared species in meat products is illegal under Food Labeling Regulations. Apart from regulatory reasons, the prevention of adulteration of meat products with less desirable meat species is important to the consumers for economic, health, food safety and religious reasons.

Several methods have been developed to identify meat species including electrophoresis, chromatography, DNA hybridization, and immunoassays. Immunological techniques, including agar-gel immunodiffusion (AGID) and enzyme-linked immunosorbent assay (ELISA) are most commonly applied for meat species identification.

There are several disadvantages to the official method AGID. Concentrated antiserum preparations are required to obtain visible precipitin lines in AGID. Obtaining the antiserum is expensive in large-scale testing. Furthermore, the sensitivity of AGID is variable. Usually ten percent or more contamination must be present to detect adulteration with this method. Lastly, AGID cannot be used for species identification in cooked meat because of the shortage of commercial antiserum specific to cooked meats.

The ELISA method has emerged as a sensitive, rapid, and specific method for meat speciation. This method can detect levels as low as one percent or less of meat contamination. Furthermore, it requires only simple sample preparation and no expensive equipment or highly skilled operator. In addition, the ELISA technique can be used for both qualitative and quantitative analysis of meat proteins.

Specific antibodies, either polyclonal antibodies or monoclonal antibodies (MAbs), are required as capture reagents in ELISA. Most of the ELISA methods currently employed for meat species identification use polyclonal antibodies as a capture reagent. However, polyclonal antibodies have disadvantages such as limited production, variable affinity and a requirement for further purification to eliminate cross-reaction.

Using MAb based ELISA can provide better data quality and eventually reduce the cost of assays. To date, the monoclonal antibodies which are utilized in ELISA based assays for meat identification have been raised against native proteins. The antibodies are useful for the detection of meat in raw meat mixtures.

A few disclosures of the production of polyclonal antibodies for the qualitative detection of meat species in cooked meat samples has been reported. These polyclonal antibodies have been raised against native heat-resistant immunizing antigens.

Wide spread meat species adulteration has been found particularly among heat-processed meat products and retail meat markets. Hsieh et al. (1995) *Jrnl. of Food Quality* 19:1-13, indicated that the violation rate in cooked products was higher than raw meats (22.9% versus 15.9%) in the domestic market. This adulteration can have serious health consequences. Poultry carries pathogens that cause food-borne diseases. Cooking poultry requires a minimum internal temperature of 71.1° C. (160° F.) to kill salmonella. Beef requires a minimum internal temperature of 68.3° C. (155° F.) to kill *E. Coli* H7:0157. If a meat product like beef is contaminated with poultry meat, it might impose a potential health hazard due to the inadequate heat-processing even at a very low level of contamination.

Additionally, regulatory controls to prevent the spread of BSE have prohibited the use of certain animal proteins in feed in several countries, requiring accurate analytical methods for detecting prohibited material in feed stuffs to ensure compliance with the new regulations. Microscopic analysis is commonly used to identify constituents of animal origin, e.g. blood clots, bone fragments, feather fragments, hair or muscle fiber, in feed stuffs. Hahn (1999) *Naturwissenschaften* 86:62-70. The method is simple and inexpensive, although it requires a certain degree of expertise to distinguish bone fragments of mammals from those of poultry and fish by observing the shape of lacunae. Methods based on PCR amplification of mitochondrial DNA have recently been developed, but generally are not able to distinguish between different tissues of the same species. Immunological methods have played a central role in the species identification of raw and heat processed meats. Hsieh et al., "Monoclonal antibodies against heat-treated muscle proteins for the species identification and endpoint temperature determination of cooked meats" *Quality attributes of muscle foods*, 1999, pp. 287-307, Plenum Publishing Co., New York, N.Y. The official enzyme immunoassay method for analyzing mammalian proteins of rendered animal material in the UK utilizes antisera raised against heat-stable proteins. Ansfield (1994) *Food & Agricultural Immunology*, 6:419-433. However, it detects most mammalian proteins without discrimination between prohibited and allowed proteins and requires the complement of microscopic analysis to confirm the presence of mammalian MBM (meat and bone meal).

Thus, development of a suitable screening method to detect undeclared exogenous meat is important to comply with the food labeling regulation and animal feed regulation. There is, therefore, needed a method for the determination of species identification in cooked meats, as well as in animal feed.

In our experience, crude thermostable immunogens could theoretically be used in the production of species-specific MAbs, but were actually ineffective because the chance of success in selecting a specific clone by screening with crude antigen is remote. The use of a defined antigen with known antigenic determinants, a so-called species marker, would substantially increase the chance of eliciting specific antibodies. Thus, besides thermostability, the selected species marker needs to possess a unique antigenic region for a given species that is not present in the counterpart molecules of other species.

SUMMARY OF THE INVENTION

The present invention is drawn to antibodies, monoclonal antibodies or fragments thereof which bind to Troponin I, a thermostable muscle protein, as well as to methods for making such antibodies and their uses. The antibodies are capable of meat species identification in raw and cooked meats and thus, find use in the detection of species substitution in meats, for determining end-point cooking temperature, and for determining the adequacy of the heat treatment of rendered meat. Additionally, because the presence of Troponin I in blood is indicative of muscle degradation, the antibodies find use in the diagnosis of skeletal muscle disease, as well. Kits containing the antibodies are also provided.

DETAILED DESCRIPTION OF THE INVENTION

The invention is drawn to the use of skeletal Troponin I (sTnI) as a thermally stable protein component of meat. Troponin I (TnI) is a 24 kD, heterogenic protein which varies immunologically between animal species. Several isoforms of TnI exist within each animal species including skeletal muscle and cardiac muscle. These different isoforms of TnI can be immunologically distinguished. The antibodies of the invention include polyclonal and monoclonal antibodies as well as fragments thereof which retain the ability to bind to at least one isoform of TnI. In one embodiment, the antibodies of the invention selectively bind to sTnI. Antibodies are also disclosed which are specific for TnI of a particular animal species of choice.

An antibody, MAb, or fragment thereof is said to be capable of binding to a molecule if it is capable of specifically reacting with the molecule to thereby bind the molecule to the antibody, MAb, or fragment thereof. The term "antibody" (Ab) or "monoclonal antibody" (MAb) is meant to include intact molecules as well as fragments or binding regions or domains thereof (such as, for example, Fab and F(ab)$_2$ fragments) which are capable of binding antigen. Such fragments are typically produced by proteolytic cleavage, such as papin or pepsin. Alternatively, antigen-binding fragments can be produced through the application of recombinant DNA technology or through synthetic chemistry.

Methods for the preparation of the antibodies of the present invention are generally known in the art. For example, see *Antibodies, A Laboratory Manual, Ed.* Harlow & David Lane (eds.) Cold Spring Harbor Laboratory, N.Y. (1988), as well as the references cited therein. Standard reference works setting forth the general principles of immunology include: Klein, J. *Immunology: The Science of Cell-Noncell Discrimination,* John Wiley & Sons, N.Y. (1982); Dennett, R. et al. *Monoclonal Antibodies, Hybridoma: A New Dimension In Biological Analyses,* Plenum Press, N.Y. (1980); and Campbell, A. "Monoclonal Antibody Technology," *Laboratory Techniques In Biochemistry And Molecular Biology,* Vol. 13, Burdon et al. (eds.), Elsevier, Amsterdam (1984). See also, U.S. Pat. Nos. 4,609,893; 4,713,325; 4,714,681; 4,716,111; 4,716,117; and 4,720,459.

The antibody and monoclonal antibodies of the present invention can be prepared by various methods. One method to obtain antibodies to TnI utilizes purified TnI from an animal species. Bovine troponin complex can be prepared from beef by modifying the method of Ebashi et al. (1971) *J. Biochem.* 69(2), 441-45, which is incorporated herein in its entirety. Generally, after removing fat and connective tissue, muscle tissue is ground and thoroughly mixed. Troponin complex is extracted and TnI, TnC and TnT is fractionated chromatographically, then dialyzed. The purified TnI can be used to immunize mice.

TnI can be purified from any animal, including pigs, sheep, cattle, horse, deer, chicken, turkey, and the like. TnI can be generally prepared from these species by affinity chromatography utilizing the calcium-dependent binding capability of bovine TnC to various TnI. See Syska et al. (1974) *FEBS Letters* 40(2):253-257, which is incorporated herein in its entirety. The purified TnI is then dialyzed and can be used to immunize mice.

Antibodies or monoclonal antibodies made by the above method can be selected by indirect ELISA. In performing the indirect ELISA assays, TnI is bound to a polyvinyl surface.

By the method of the invention described herein, monoclonal antibodies having a desired specificity can be selected. Thus, monoclonal antibodies specific for a particular meat species or for a type or class of meats can be produced.

By meat type or class is intended a broader class of meats including several meat species. Thus, type or class refers to mammalian, avian, poultry, and the like. By meat or meat species is generally intended meats which are commonly used for consumption, including poultry such as chicken, turkey, and duck, and mammalian meats, such as pork, beef, lamb, deer, and horse. Thus, particular meat species include but are not limited to chicken, turkey, duck, pork, beef, lamb, deer, horse, fish, shellfish, and the like. It is recognized that the method of the invention could be utilized to obtain antibodies against any meat species.

The methods of the invention can be used to develop antibodies which are capable of identifying classes of muscle, for example, mammalian verses poultry, as well as to identify the particular muscle species, for example, pig versus chicken. In this manner, the antibodies of the invention are useful for muscle type or class as well as particular muscle species identification. Such antibodies are capable of binding to both cooked and raw meat samples. Thus, these antibodies are useful for identification of meats in both raw and cooked meat samples.

By meat is intended flesh of animals including, but not limited to, chicken, turkey, duck, pork, beef, lamb, deer, horse, fish, shellfish, and the like.

Because the antibodies are both muscle and class specific, they are useful in the detection of species substitution in meats. To facilitate their use, kits containing the antibodies can be made. The antibodies can be coated onto a solid phase, such as ELISA microliter plate, dipstick, lateral flow, magnetic beads, and the like, and used as a sensitive reagent to accurately detect a meat of interest in both cooked and raw meat products. This commercial kit form is useful for rapid and convenient use by regulatory agencies and the meat industry. By "kit" is intended that the MAb and any necessary reagents are contained in close confinement in the form of a ready-to-use test kit. The antibodies of the invention are usefull in non-competitive ELISA, including double-sandwich ELISA assays as well as competitive assays. However, other formats such as homogenous enzyme immunoassays or immunosensors may be developed. In addition, the MAbs can be used to identify the presence of muscle in other biological samples, such as blood or urine.

Embodiments of the invention include monoclonal antibodies which have been developed using purified TnI as the antigen. An "isolated" or "purified" protein, or immunologically active portion thereof, is substantially or essentially free from components that normally accompany or interact with the protein as found in its naturally occurring environment. Thus, an isolated or purified protein is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or immunologically active portion thereof is recombinantly produced, preferably culture medium represents less than about 30%, 20%, 10%, 5%, or 1% (by dry weight) of chemical precursors or non-protein-of-interest chemicals.

The hybridoma cell lines, 2G3, 1F9, 8A12, 2A8, 5G9, 1B2, 4G4, 5G8, and 6G1, were utilized in the present invention. Hybridoma cell lines 2G3 and 2A8 were deposited with the Patent Depository of the American Type Culture Collection (ATCC), Manassas, Va., on Oct. 23, 2001, and assigned Patent Deposit Nos. PTA-3782 and PTA-3783, respectively. Hybridoma cell lines 1F9 and 8A12 were also deposited with the Patent Depository of the ATCC, Manassas, Va., on Mar. 8, 2007, and assigned Patent Deposit Nos. PTA-8208 and PTA-8209, respectively. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

In one embodiment, monoclonal antibodies specific to various classes or types of raw or cooked meat have been developed. These monoclonal antibodies represent several groups of cell lines, or individual cell lines, that secrete monoclonal antibodies to specifically react with TnI from particular species, classes or types of meat tested. The first group, Group I, are represented by the MAb 2G3, produced by hybridoma cell line 2G3, deposited with ATCC as PTA-3782, which reacts with all sTnI tested, including pork, beef, lamb, horse, deer, chicken, turkey, duck, goose, ostrich, and catfish. The MAb can be used as a capture reagent in ELISA to detect any of these meats in a sample. The MAb is particularly useful to identify meat adulteration of any of these meats in an animal feed product. Additionally, the MAb is particularly useful as a capture antibody in a double sandwich ELISA. Also included in Group I are monoclonal antibodies produced by hybridoma cell line 1F9, which reacts with both sTnI (skeletal) and cardiac TnI from all species tested, including pork, beef, lamb, horse, deer, chicken, turkey, duck, goose, ostrich, and catfish. This MAb can be used as a capture reagent in ELISA to detect any of these meats in a sample, including meat of cardiac origin.

The second group of monoclonal antibodies, Group II, are represented by 8A12, produced by hybridoma cell line 8A12, and react with porcine, bovine, ovine, equine, and deer TnI. They are useful to distinguish mammalian tissue from other non-mammalian meats.

The third group of monoclonal antibodies, Group III, represented by the MAb 2A8, produced by hybridoma cell line 2A8, deposited with ATCC as PTA-3783, react with bovine, sheep, and deer TnI and are therefore capable of distinguishing between ruminant animal meats and that of other animal meats including, but not limited to, horse, chicken, turkey, duck, goose, ostrich, and catfish.

A fourth group of monoclonal antibodies, represented by the MAbs 5G9 and 1B2, produced by hybridoma cell lines 5G9 and 1B2, respectively, react with bovine and sheep TnI and are therefore capable of distinguishing bovine and sheep meat from that of other animal meats including, but not limited to, horse, chicken, turkey, duck, goose, ostrich, and catfish.

Individual cell lines include 4G4, produced by hybridoma cell line 4G4, which reacts with poultry TnI, but not with other meat species.

Another individual cell line includes 5G8, produced by hybridoma cell line 5G8, react with chicken and turkey TnI, but not with other meat species.

An additional cell line is represented by 6G1, produced by hybridoma cell line 6G1, which reacts with equine TnI, but not with other meat species.

All groups of monoclonal antibodies react with TnI from both cooked and raw meat products.

U.S. Pat. No. 6,288,215, issued to Y. H. Peggy Hseih and pending U.S. patent application Ser. Nos. 09/225,141 and 09/963,986, and International Patent Application No. PCT/US97/15281 disclose MAbs 1A5, 2E2, 2F8, 3E12, 5D2, 5H8, 5H9, 6F7, 6G8, and 8A4 which bind to heat stable proteins. At the time of that application, it was not known what heat stable was the antigen. To the extent that any of the MAb of U.S. Pat. No. 6,288,215, pending U.S. patent application Ser. Nos. 09/225,141 and 09/963,986, and International Patent Application No. PCT/US97/15281 bind TnI, they are not included in the present invention. Thus, the present application is drawn to antibodies that bind TnI, but not MAbs 1A5, 2E2, 2F8, 3E12, 5D2, 5H8, 5H9, 6F7, 6G8, and 8A4.

The antibodies of the present invention are also useful for the detection of muscle protein in blood, urine, and other biological samples. Thus, the antibodies of the present invention are useful in detecting and monitoring diseases of or damage to an organism's muscle tissue. See, e.g., Takahashi et al. (1996) Clin. Biochem. 29(4):301-8 and Prellwitz et al. (1996) Med. Klin. 91(6):336-42.

The antibodies of the invention also find use in the determination of end-point temperature of a cooked meat sample. Inadequate cooking is an important contributing factor in food-borne disease outbreaks caused by meat products. For this use, antibodies are developed against heat-denatured or heat degraded soluble proteins. Heat induces conformational changes of the protein molecules. In this manner, end-point temperature can be determined by using the antibody in an ELISA to detect the immunoreactivity changes of the heat treated muscle proteins. An increase in reactivity is noted due to increased heating process of the meat sample. The antibody allows for a means to determine end-point temperature to which meats have been processed.

The following experiments are offered by way of illustration and not by way of limitation.

EXPERIMENTAL

EXAMPLE 1

Identification of TnI as a Thermostable Species Marker Protein

Applicants have previously produced several porcine-specific MAbs raised against crude porcine protein extract for the detection of pork in both raw and cooked meats. See Chen et al. (1998) *J. Food Sci.* 63(2):201-205. See also U.S. Pat. No. 6,288,215 and U.S. patent application Ser. Nos. 09/225,141 and 09/963,986, each of which is incorporated herein by reference. These MAbs, particularly MAb 5H9, recognize a 24 kD thermostable skeletal muscle protein (TSMP) which is porcine skeletal-muscle specific. Applicants theorized that the purified protein could serve as an ideal marker for meat speciation and detection. Recently, Applicants identified the porcine protein as a member of the Troponin complex (TnI, TnC, and TnT), Chen et al. (2001) *J. of Food Sci.* 66(6):799-803, specifically porcine TnI. See also Chen et al. (2002) *Meat Sci.* 61:55-60.

The following example demonstrates the thermostability of TnT and its usefulness as a meat speciation marker.

Materials and Methods

Purification of TnI

Pork ham, beef round, leg of sheep, and turkey and chicken thigh were obtained from Auburn University Meat Laboratory. Horse and deer round and ostrich thigh were received from Auburn University College of Veterinary Medicine. All meats were at least 24-h postmortem and without previous freezing and processing. After removing external fat and connective tissues, skeletal muscles from the leg portions were finely ground and thoroughly mixed. All utensils were completely cleaned before muscles of different species were processed. The mixtures were divided into aliquots and stored at 80° C.

Bovine troponin complex was extracted from skeletal muscle by 0.8 M LiCl according to the method of Ebashi et al. TnI, TnC and TnT were fractionated by diethylaminoethyl cellulose (DE52, Whatman, Fairfield, N.J.) followed by carboxymethyl cellulose (CM52, Whatman) chromatography according to the method of Perry and Cole (1974) *Biochem. J.* 141(3):733-743.

TnIs of other species (porcine, ovine, equine, deer, chicken, and turkey) were purified individually from skeletal muscle by an affinity chromatography, Syska et al., utilizing the calcium-dependent binding capability of bovine TnC to various TnIs. Purified TnIs were dialyzed in 0.01 M sodium phosphate containing 0.5 M NaCl. Purity of TnI from different species was examined by sodium dodecyl sulfate-polyacrylamide gel electrophoresis (SDS-PAGE) which showed a major band at 24 kD from all the preparations. Protein concentrations of the purified TnIs were determined by Bio-Rad Protein Assay (Catalog No. 500-0006; Bio-Rad, Hercules, Calif.) using bovine serum albumin (BSA) as the standard.

Preparation of Raw and Cooked Porcine Muscle Extracts

Ground porcine muscles (10 g) were packed into the bottom of capped glass tubes. For cooked samples, tubes were placed in boiling water for 30 min, then chilled immediately in ice water. Tubes of raw and cooked samples were individually homogenized in 20 ml of 0.5 M sodium chloride using a Polytron homogenizer (Model PT 10/35; Brinkmann Instruments Co., Westbury, N.Y.). Samples were set in a refrigerator for 1 h with constant stirring, then centrifuged (15,000×g) at 4° C. for 30 min. The supernatant was filtered through a Whatman No. 1 filter paper and stored at −80° C.

Preparation of MAb

The MAb used in this study, MAb 5H9, has previously been described. See U.S. Pat. No. 6,288,215 for availability and deposit information. Ascites fluid of MAb 5H9 was obtained from mice injected peritoneally with the antibody-secreting hybridoma cells. Immunoglobulin G (IgG) was separated from the ascites fluid using a Protein A Cartridge with a MAPS II buffer (Catalog No. 156-0006 & 153-6164, Bio-Rad). The purified antibody was dialyzed against phosphate buffered saline (0.01 M sodium phosphate and 0.15 M sodium chloride, pH 7.2) overnight at 4° C. with several changes of the dialysis buffer. Purity of the antibody was checked by sodium dodecyl sulfate-polyacrylamide gel electrophoresis (SDS-PAGE) and the concentration of IgG in the final preparation was determined by UV absorption at 280 nm.

Gel Electrophoresis and Immunoblot

SDS-PAGE was carried out on discontinuous polyacrylamide gels (Laemmli, 1970) with stacking gels (4% T; 2.67% C) and separating gels (12% T; 2.67% C) using a Mini-PROTEAN II electrophoresis cell (Bio-Rad). For the 2-D gel electrophoresis, samples were first separated by the non-equilibrium pH gradient gel electrophoresis (NEPHGE) as described by O'Farrell, Goodman, and O'Farrell (1977) using a Mini-PROTEAN II tube cell. The capillary gels were then loaded onto slab polyacrylamide gels and SDS-PAGE was carried out with stacking gels (4% T; 2.67% C) and separating gels (15% T; 2.67% C). Gels were stained with Coomassie Brilliant Blue G-250. For immunoblotting, proteins were electrotransferred (1 h at 100 V) from polyacrylamide gel to nitrocellulose membrane using a Mini Trans-Blot unit (Bio-Rad) with transfer buffer containing 25 mM Tris, 192 mM glycine and 20% methanol, pH 8.3 (Towbin, Staehelin, & Gordon, 1979). Antigenic components on the membrane were subsequently detected by MAb 5H9 according to Chen et al. (1998).

Enzyme-linked Immunosorbent Assay

Indirect ELISA employing MAb 5H9 as the detection reagent was performed using previously described procedures, Chen et al. (2000) *J. AOAC Int'l.* 83(1):79-85. See FIG. 3. The protein concentrations used to coat the wells of the microtiter plates were as indicated in corresponding figures. The detection limit of ELISA was determined (three standard deviations above the zero-dose response ) as 5 ng/ml of porcine sTnI.

Heat Treatment of Troponin I

Porcine sTnI was dissolved in phosphate buffered saline (0.01 M sodium phosphate and 0.15 M sodium chloride, pH 7.2) to a concentration of 0.1 mg/ml. The solution was passed through a 0.45 micron syringe filter (Corning Lab Co., Corning, N.Y.), then dispensed into 0.5 ml flat-cap, thin-wall polypropylene reaction tubes (MJ Research, Inc., Watertown, Mass.). Triplicate samples were then subjected to different prescribed heat treatments (isothermal water bath at 80° C. for 30 min, boiling water bath at 100° C. for 30 min, autoclave at 121° C. for 30 min, and at 126° C. for 120 min). After heating, the tubes were immersed in ice water for 5 min. and centrifuged at 14,000 g for 30 min. The soluble protein concentration of the supernatant was analyzed in four repeated measurements using Bio-Rad Protein Assay and the antigenicity of heat-treated TnI to MAb 5H9 was evaluated by indirect ELISA. Data were statistically examined by analysis of variance using SASTM procedures, and the differences among means were compared using Duncan's multiple range test ($P<0.05$).

Results and Discussion

Comparison of Thermostable Skeletal Muscle Protein and Porcine TnI

Figure 1:
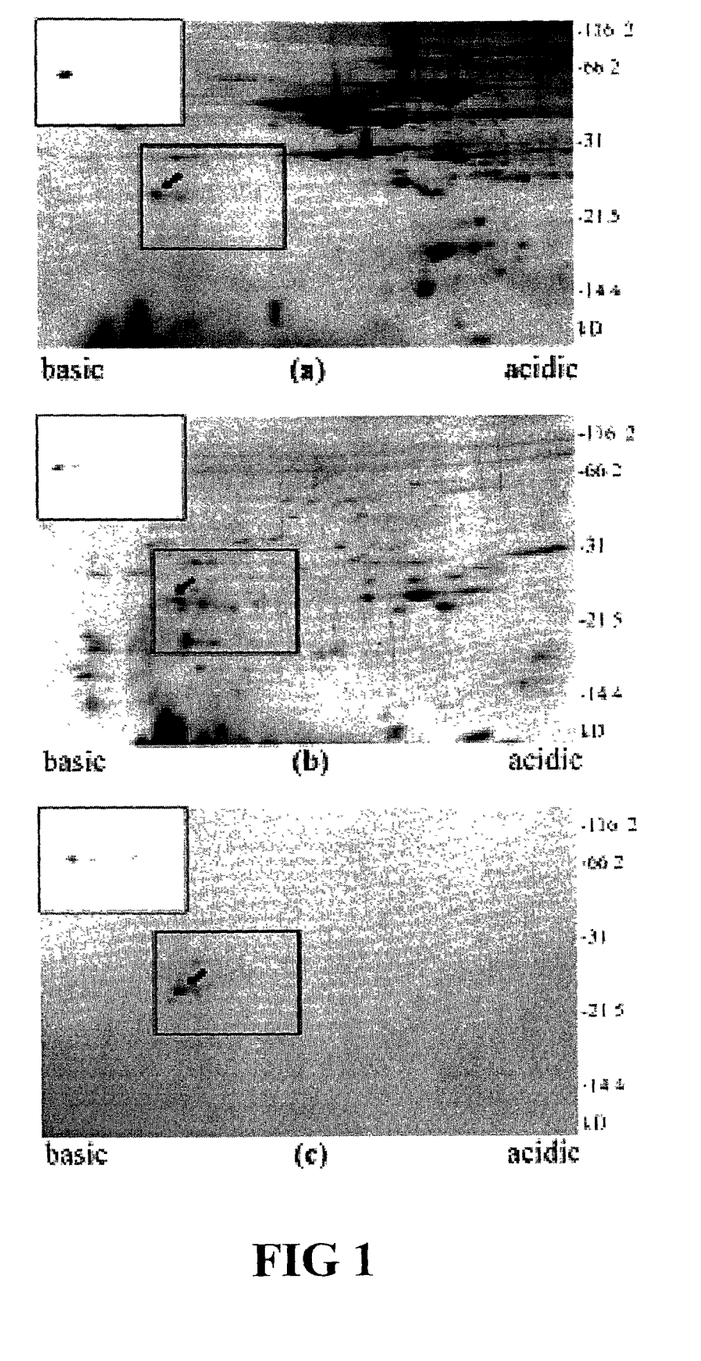
FIG. 1. Two-D gel electrophoresis and immunoblot using MAb 5H9: (a) raw pork extract, (b) cooked pork extract, (c) isolated porcine skeletal TnI. Immunoblot corresponding to the framed area on each gel is presented at the top left corner. Quantities of total protein in the gels were 40, 12, and 1 mg, respectively. Experimental details are set forth in Example 1 (below).

Correspondence of 24 kD TSMP in raw and cooked pork extracts to the isolated porcine sTnI was elucidated by their concurrent electrophoretic mobility on 2-D gels. Both TSMP and sTnI are strong basic proteins; therefore, the separation included NEPHGE in the first dimension, which permits the separation of basic proteins in capillary glass tubes using conventional carrier ampholytes, and SDS-PA GE in the second dimension. Most of the proteins in the raw muscle extract clustered on the acidic side; only a few proteins migrated to the basic region (FIG. 1A). MAb 5H9 located the presence of the TSMP in the basic region and several isoelectric isoforms of this protein scattered out towards the acidic side. These results confirmed the earlier observation that TSMP consists of several isoelectric variants, which may result from the small fraction of the protein with various degrees of phosphorylation, Chen et al. As shown in FIG. 1B, the MAb 5H9 also revealed the presence of the TSMP in the cooked meat extract at the same location within the basic region as that in the raw meat extract, indicating that the heat treatment did not degrade this protein. In contrast, most of the proteins on the acidic side faded as a result of heat denaturation. In addition, the cooked meat extract contained several basic proteins which were not seen in the raw extract. The presence of these basic proteins can be explained as being a result of fragmentation of larger proteins during heating, as discussed in an earlier paper, Chen et al. (2001) *J. Food Sci.* 66(6):799-803. As expected, TSMP probed by MAb 5H9 displayed an identical pattern to that seen in the raw muscle extract. Moreover, the isolated sTnI from porcine skeletal muscle showed exactly the same pattern and location as the TSMP seen in the raw and cooked muscle extracts (FIG. 1C). These results clearly indicate the correspondence of TSMP to sTnI, confirming that the 24 kD TSMP present in pork extracts is sTnI. The molecular specificity of MAb 5H9 to porcine sTnI confers the necessary specificity of ELISA for the detection of pork in various cooked meat products, Chen et al.

Specificity of MAb 5H9 to Porcine TnI

Figure 2:
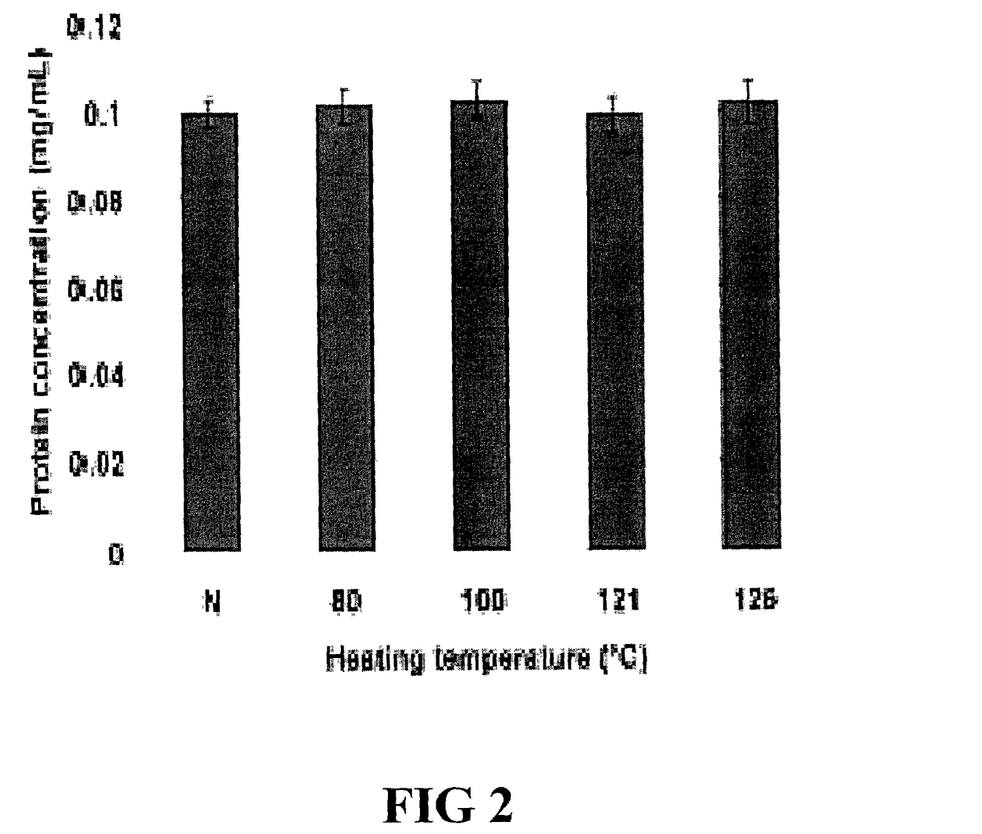
FIG. 2. Soluble protein concentration of heat-treated porcine sTnI. Data represent means of three replications and error bars indicate +/− one standard deviation. The initial protein concentrations of sTnI in each treatments were 0.1 mg/ml as determined by Bio-Rad Protein Assay using bovine serum albumin as the standard. Unheated sTnI (N) and heated sTnI (80, 100, or 121° C. for 30 min or 126° C. for 120 min). See Example 1 (below).

The reactivity of MAb 5H9, which is specific to the 24 kD TSMP, to individual components of porcine skeletal troponin (sTnT, sTnI, sTnC) and cardiac TnI, along with TnI from bovine and chicken skeletal muscle, was evaluated by indirect ELISA and immunoblot. From the results of ELISA, MAb 5H9 recognized native porcine sTnI adsorbed on the plastic surface of microtiter plates (FIG. 2). There was no reaction of MAb 5H9 to other skeletal troponin components (sTnT and sTnC) or to the cardiac isoform (cTnI).

Thermal Stability of TnI

Figure 3:
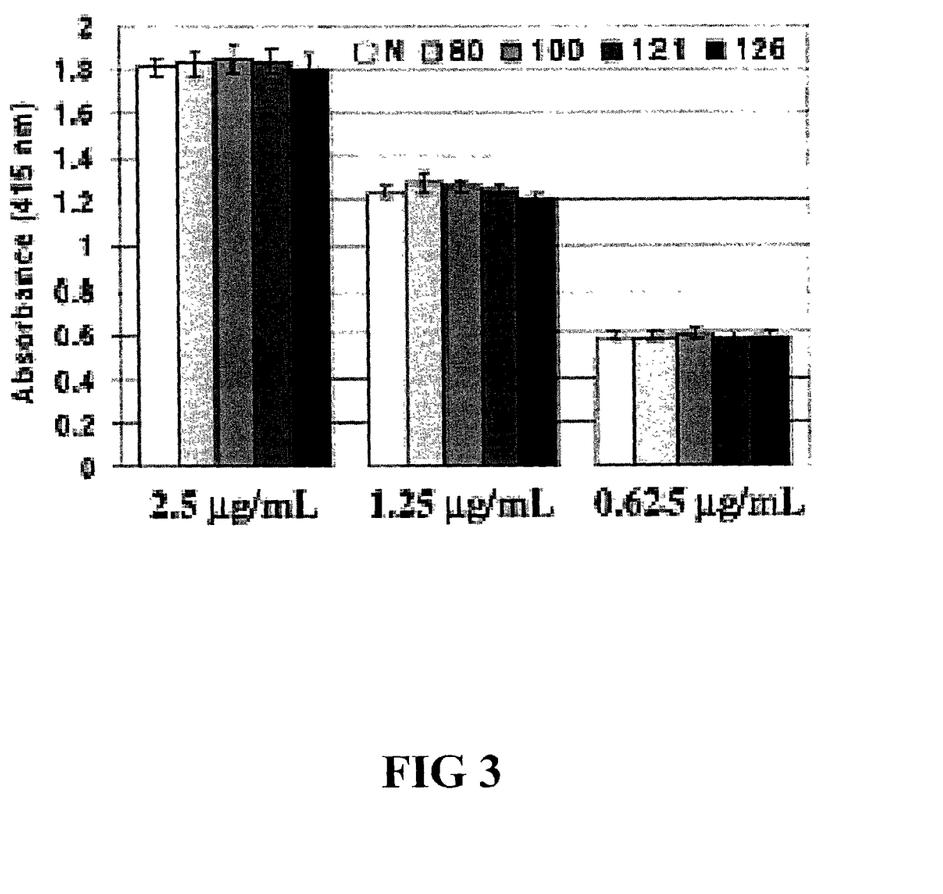
FIG. 3. ELISA response of heat-treated porcine sTnI. Microtiter plates were coated with sTnI from the different heat treatments at concentrations of 2.5, 1.25, and 0.625 mg/ml. Data represent means of three replications and error bars indicate +/− one standard deviation. Unheated sTnI (N) and heated sTnI (80, 100, or 121° C. for 30 min or 126° C. for 120 min).

Porcine sTnI retained its solubility after various heat treatments (80, 100, and 121° C. for 30 min and 126° C. for 120 min), as the concentration of sTnI in the solutions remained unchanged (FIG. 2), with a mean=0.101 mg/ml and S.D.=0.0 03 mg/ml among treatments. There was no difference in the ability of MAb 5H9 to recognize heat-treated sTnI as measured by ELISA at three concentration levels (FIG. 3). Also, the heat-treated sTnI showed an identical profile (gels not shown) to that of unheated sTnI on the 2-D electrophoresis (shown in FIG. 1c). These results indicate little change in the solubility and antigenicity of porcine sTnI during heating.

EXAMPLE 2

Generation of Monoclonal Antibodies to TnI

Purification of TnI

Purification of TnI was carried out as described in Example 1, above.

Immunization

Bovine TnI (1.0 mg/ml) dissolved in phosphate buffered saline (PBS, 0.01 M sodium phosphate and 0.15 M sodium chloride, pH 7.2) containing 0.3% of SDS was heated in boiling water for 30 min. Four BALB/c mice (7-10 weeks old) were immunized either subcutaneously or intraperitoneally with 150 mg of the heat-treated TnI mixed 1:1 (v/v) with Freund=s complete adjuvant followed by two booster injections at 4-week intervals with 100 mg/mouse of TnI mixed 1:1 (v/v) with Freund=s incomplete adjuvant.

Production of Monoclonal Antibodies

Test sera were collected by tailbleeding 10 days after each injection; the titer of the sera was then determined by indirect ELISA. The mouse exhibiting the highest serum titer to bovine TnI then received a final boost of 100 mg of the antigen in PBS, 4 days before the fusion. After the final booster, the injected mouse was sacrificed, and the spleen was harvested. The general procedures described by Kohler and Milstein (1975) were followed, with modifications as specified. Cells were washed from spleen by wash media (RPMI-1640 serum free medium supplemented with 1% oxaloacetate, pyruvate, and insulin (OPI) containing 1% glutamine, and 1% penicillin and streptomycin (p/s)) (Sigma). Cells of the murine myeloma cell line, P3×63, Ag8.653, ATCC CRL 1580 were retrieved from liquid nitrogen and cultured in large tissue culture plates (Corning, Corning, N.Y.). The culture procedure is described in Procedure A (page 31). Spleen cells from the selected mouse were fused with the myeloma cell line (P3×63.Ag8.653., ATCC CRL 1580) at a ratio of 5:1 in the presence of polyethylene glycol (MW 4000). One ml of 50% PEG was gently added to the cells dropwise. After standing for one minute, 30 ml of wash media was added to cells dropwise. The fused cells were resuspended in Hypoxanthine-aminopterin-thymidine (HAT) selective growth medium (RPMI-1640 supplemented with 15% fetal bovine serum (FBS), 1% OPI, 1% glutamine, 1% p/s, 1% HAT) (Sigma) and seeded in 96-well tissue culture plates that have been set with mouse thymocyte feeder cells (Kohler and Milstein, 1975). The hybridoma cells were incubated at 37° C. with 5% $CO_2$ (Napco $CO_2$ incubator model 6300, Tualatin, Oreg.). The medium was changed twice to remove residual antibodies before the initial screening against bovine TnI using indirect ELISA. For a secondary selection, the positive cells from the initial screening were transferred to larger wells and cultured for 3 more days before testing for cross reactivity with TnIs from other species. In this way, hybridomas with distinct reaction patterns to heterologous TnI were selected.

Antibody-producing hybridoma cells of interest were selected and recloned twice by limiting dilution (Campbell, 1991) and the isotypes of the antibodies secreted by the cell lines were determined using the immunoType isotyping kit according to manufacture's manual (Sigma). Cells were diluted with complete growth media (RPMI-1640 supplemented with 15% FBS, 1% OPI, 1% glutamine and 1% p/s) to give a concentration of 0.5 or 1 cell per well. Two hundred μl of each dilution were plated in each well to 96-well plates seeded with mouse thymocyte feeder cells. The subcloned hybridoma cells were screened using the method described previously.

The antibody-producing hybridoma cells were expanded from 96-well plate to 48-well plate. When the cells grew heavily in the well, they were expanded to 24-well plate, 12-well plate, small petri culture dish and large petri culture dish, sequentially. When cells grew heavily in the large petri dish, they could be frozen and stored in liquid nitrogen (Procedure B, page 32).

Ascites fluids of MAbs were obtained from Pristane primed mice 10-14 days after intraperitoneal injection of the hybridoma cells. Antibodies were separated from the ascites fluid using a Protein A Cartridge with MAPS II buffer (Bio-Rad, Catalog No. 156-0006 & 153-6164). The purified antibodies were dialyzed against PBS overnight at 4 □C with several changes of dialysis buffer. The concentration of IgG in the final preparation was determined by UV absorption at 280 nm. The purified MAbs were titrated against bovine TnI by indirect ELISA.

ELISA

For primary hybridoma screening and MAb titration, polyvinylchloride microtiter plates (Costar, Cambridge, Mass.) were coated with bovine TnI (0.2 mg/ml) in carbonate buffer (pH 9.6), and blocked with 1% of BSA in PBS.

For secondary cross-species screening, the plates were coated with TnI from different species (porcine, bovine, ovine, equine, deer, chicken and turkey). Either culture supernatant or series diluted MAbs in antibody buffer (1% BSA in PBS containing 0.05% of Tween20) were added to the wells and incubated for 1 h at 37° C. followed by the addition and incubation of goat anti-mouse IgG peroxidase conjugate (Bio-Rad, 1:3000 diluted in antibody buffer). Plates were washed three times with PBS containing 0.05% of Tween20 between each step. The bound enzyme activity was revealed by the addition of the enzyme substrate (22 mg of 2,20-azino-di-[3-ethyl-benzothiazoline-6-sulfonic acid] and 15 ml of 30% hydrogen peroxide in 100 ml of 0.1 M phosphate-citrate buffer, pH 4.0). The reaction was stopped after 10 min by the addition of 0.2 M citric acid. Color developments were evaluated spectrophotometrically at 415 nm using a microplate reader (Bio-Rad, Model 450).

SDS-PAGE and Western Blot

Sodium dodecyl sulfate-polyacrylamide gel electrophoresis (SDS-PAGE) was performed to resolve the protein extracts of different cooked meat species. Western blot was then carried out to transfer proteins from gel to nitrocellulose membrane and to determine the molecular weights of immunogenic components which reacted with developed MAbs. Sodium dodecyl sulfate-polyacrylamide gel electrophoresis was performed according to the method of Laemmli (1970) with the following modifications. Proteins were separated on 4% acrylamide stacking gel (pH 6.8) and a 12% acrylamide separating gel (pH 8.8). The protein extracts of different cooked meat species were diluted one-half with sample buffer containing 2% (wt/vol) SDS, 5% (vol/vol) β-mercaptoethanol, 60 mM Tris hydrochloride (pH 6.8), 25% (vol/vol) glycerol and 0.0001% (wt/vol) bromophenol blue (Laemmli, 1970), boiled for 2 minutes, cooled, and applied to the gel at 10 μg/well. The gel was electrophoresed at 200 V for 45 minutes using a Protean-II minigel system (Bio-Rad) connected to a power supply (Bio-Rad Model 3000). After electrophoresis, the resolved protein bands were transferred to nitrocellulose membranes (Bio-Rad) at 100 V for 1 hour using an electroblotting apparatus (Bio-Rad) in blotting buffer (20 mM Tris, 250 mM glycine, 20% methanol) according to the method of Towbin et al. (1979). Upon completion of the electroblotting, the nitrocellulose membrane was blocked by 3% gelatin (Bio-Rad) in PBS for 30 minutes. Following two washes in Tris-buffered saline with Tween (TBST) (TBS, pH 7.5, containing 0.05% Tween-20), the membrane was incubated with hybridoma supernatant in antibody buffer (1% gelatin in TBST) overnight at room temperature. The excess MAb was removed by washing twice with TBS, and the membrane was incubated with goat anti-mouse IgG alkaline phosphatase conjugate diluted in antibody buffer (1:3000) for 1 hr at room temperature. After washing with TBST two times, and an additional wash with TBS, the membrane was incubated with 5-bromo-4-chloro-3-indolyl phosphate/p-nitroblue tetrazolium chloride (BCIP/NBT) in alkaline phosphatase color development solution (0.1 M, pH 9.5 Tris buffer)(Bio-Rad). The reaction was stopped by washing the membrane in distilled water. The appearance of a dark purple band indicated the antibody binding site. The prestained PAGE broad range standards including myosin (M. Wt. 205,000), β-galactosidase (M. Wt. 116,500), bovine serum albumin (M. Wt. 80,000), ovalbumin (M. Wt. 49,500), carbonic anhydrase (M. Wt. 32,500), soybean trypsin inhibitor (M. Wt. 27,500), lysozyme (M. Wt. 18,500) and aprotinin (M. Wt. 6,500) were used as molecular weight markers in SDS-PAGE and Western immunoblotting.

Isotyping of MAb

The isotype of MAb was determined by a mouse MAb isotyping kit according to manufacture's manual (Sigma).

Results and Discussion

Production and Characterization of Anti-TnI MAbs

From two consecutive fusions, the overall positive rate was around 10% of the original fusion wells when first screened against bovine TnI. After the supernatant from positive wells was retested against heterologous TnI for cross-species reactivity, several cell lines secreting MAbs with distinct patterns were selected. These MAbs were categorized into three groups according to their reactivities to heterologous TnI (above). The characteristics of these MAbs are summarized in Table 1. The first group includes three MAbs (1F9 and 2G3) which displayed a broad reactivity to all the TnIs from porcine, bovine, ovine, equine, deer, chicken, turkey, duck, goose, ostrich, and catfish. The second group includes MAbs, such as 8A12, which reacted to TnI of mammalian species only (porcine, bovine, ovine, equine, deer). The third group includes an MAb (2A8), which recognized specifically TnI of ruminant species (bovine, ovine, deer).

TABLE 1

Characteristics of anti-troponin I monoclonal antibodies

| Group | MAb | Isotype | Species specificity[a] | Titer (ng/ml)[b] |
|---|---|---|---|---|
| I | 1F9 | IgG1 | P, B, S, H, D, C, T, K, G, O, F[c] | 5.2 |
|  | 2G3 | IgG1 | P, B, S, H, D, C, T, K, G, O, F | 6.1 |
| II | 8A12 | IgG1 | P, B, S, H, D | 11.1 |
| III | 2A8 | IgG1 | B, S, D | 10.5 |

[a]Species specificities of the MAbs were determined by both indirect ELISA and immunoblotting.
[b]Titers were expressed as the antibody concentration (ng/mL) at 50% maximum binding to bovine troponin I in the indirect ELISA as described in Section 2.4.
[c]P = porcine; B = bovine; S = sheep; H = horse; D = deer; C = chicken; T = turkey; K = duck; G = goose; O = ostrich; F = catfish.

Cell lines secreting IgG were chosen because of its ease of handling and good performance in immunoassay. The isotypes of the MAbs all belong to IgG1.

The use of heat-treated TnI as the immunogen but native TnI for ELISA screening ensures that the selected MAbs, which recognize heat resistant epitopes appearing on both native and heat-treated antigen molecules, are capable of recognizing TnI in both raw and heat-processed muscles. Titer of the MAbs, determined by indirect ELISA as the antibody concentration (ng/ml) at a level of 50% of the maximum binding to a predetermined concentration of bovine TnI, may reflect the relative affinity of the antibodies toward the same antigen, Liddell et al. "Characterization, purification, and labelling," *A practical guide to monoclonal antibodies,* 1991, pp. 105-138, John Wiley, New York. When the titer was compared among the three groups, the MAbs of Group I always showed the highest titer, whereas the MAbs of Groups II and III exhibited only slight differences.

Identification of TnI in Heat Treated Muscles

Figure 4:
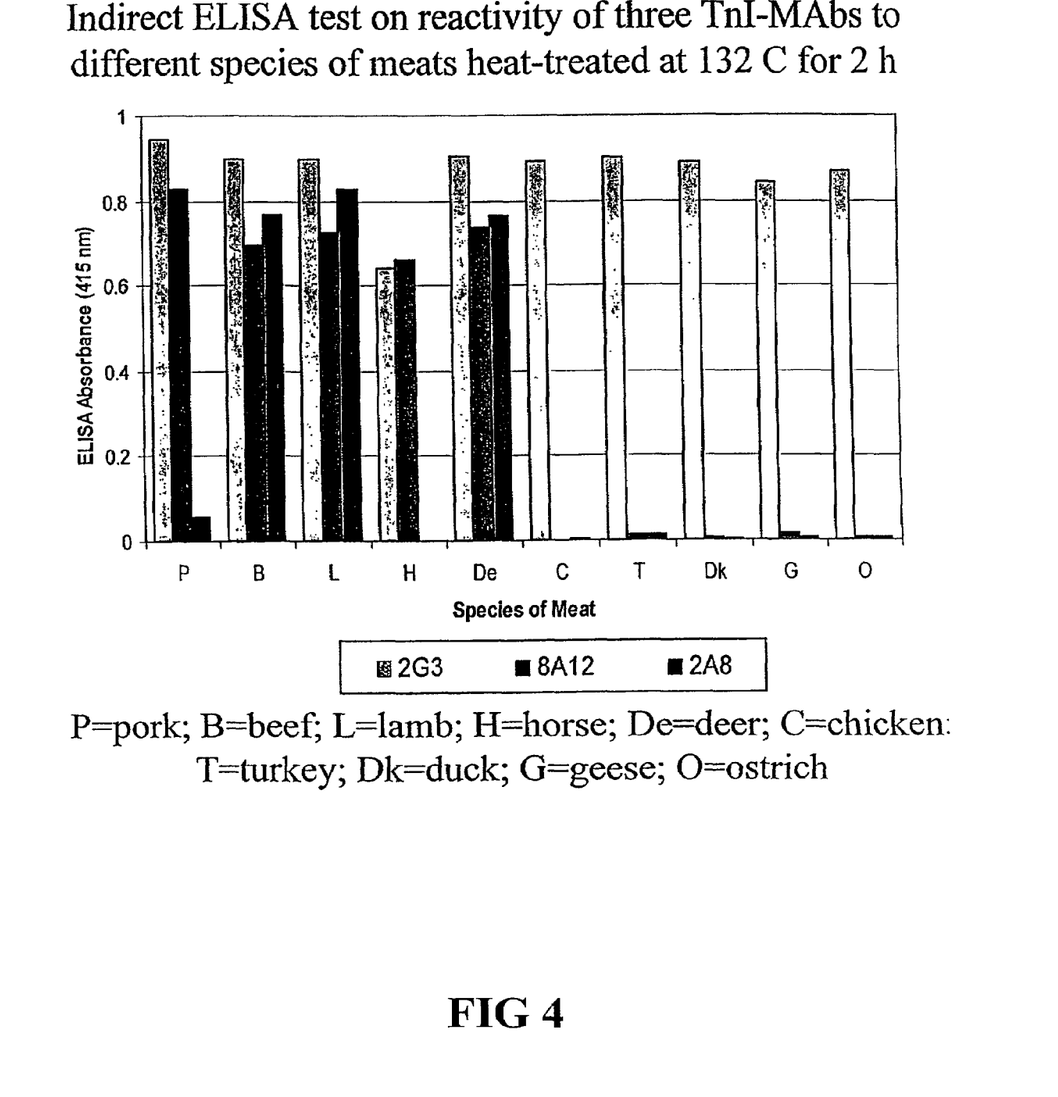
FIG. 4. Specific reactivity of indirect ELISAs to meat samples produced from heated muscles (132° C., 2 hours) of a single animal species. P=pork; B=Beef; L=Lamb; H=Horse; De=Deer; C=Chicken; T=turkey; Dk=Duck; G=geese; O=ostrich.

Species specificity of the MAbs to TnI was further evaluated by immunoblot of muscle extracts from different species separated by SDS-PAGE (not shown). TnI in the extract of autoclaved (121° C., 20 min) muscles was revealed by Group I MAbs as a major band around 24 kD for all species including porcine, bovine, ovine, equine, deer, chicken, turkey, duck, goose, ostrich, and catfish. Species specificity of Group II MAbs to mammalian TnI and Group III MAb to ruminant TnI by immunoblotting using muscle extracts (not shown) corresponded with the results of indirect ELISA using isolated TnI (Table 1). Abundance of TnI in skeletal muscles and its solubility after severe heating (121° C., 20 min) justify the use of TnI as a suitable marker protein for authentication of species origins of heat-processed muscles. This was confirmed by indirect ELISA testing reactivity of three TnI MAbs to different species of meat that had been heat-treated at 132° C. for 2 hours. See FIG. 4. As can be seen, reactivity remains much the same as set out in Table 1.

Current EU wide feed controls have prohibited the use of processed animal proteins to feed animals that are intended for food production. Group I MAbs, which provide broad cross-reactivity among all the species tested, including five mammalian, five avian, and one fish species, would allow the detection of muscle tissues of both territorial and marine animals. Group II MAbs, which differentiate mammalian from poultry and marine species, are capable of detecting the mammalian MBM that, under the new UK regulations, is now prohibited in feed for all farmed livestock. Where porcine and equine proteins are allowed in ruminant feeds, as permitted by the current US regulations, Group III MAb, which reacts with ruminant animal muscles (bovine, ovine, deer), would provide a means to distinguish between prohibited and allowed species. Potential applications of these MAbs in feed detection include an analysis for meat meals, meat and bone meals, animal meal, and other compound feed stuffs containing materials derived from muscle tissues.

EXAMPLE 3

Adulteration of Feed Samples

Materials and Methods

Purification of TnI

Purification of TnI was carried out as described in Example 1, above.

Immunization

Immunization was carried out as described in Example 2, above.

Production of Monoclonal Antibodies

The monoclonal antibodies used in Example 2, above, were used in the present experiment.

ELISA

Primary and secondary screening were carried out as described in Example 2, above.

The assay was further optimized for the detection of muscle tissue in feed samples. The microplates were coated with extracts from meat meals or feed samples diluted 1:20 (v/v) in carbonate buffer and blocked with 1% of BSA in PBS. MAb 2A8, or an alternative, diluted in antibody buffer (1 mg/ml) were added to the wells and incubated at 37° C. for 1 h. The rest of the procedures were the same as described above.

SDS-PAGE and Western Blot

Sodium dodecyl sulfate-polyacrylamide gel electrophoresis (SDS-PAGE) was carried out as described in Example 2, above.

Preparation of Meat Meals and Adulterated Feed Samples

Meat meals composed of single species were produced in our laboratory. Ground muscles of beef, pork, sheep, horse, deer, chicken, turkey, and catfish were placed in beakers and covered loosely with aluminum foil. The muscles were autoclaved at 132° C. and 2 bar for 2 h, then the meat slurries were dried on sheets of aluminum foil in a convection oven at 80° C. for 24 h. Dry weights of the final products ranged between 23 and 27% of the original material. Dried meats were crumbled into fine granules with a food processor; then individually packed in sealed plastic bags and stored at 4° C.

Three commercial feeds containing no animal proteins were used as the matrixes for addition of meat muscles. These animal feeds were: (1) Purina Natural Beef Builder Coarse (Purina Mills, Inc. St. Louis, Mo.) containing processed grain by-product, roughage products, grain products, plant protein products, and molasses products with various vitamins and mineral supplements, (2) Chicken Scratch Feed (Southern States Cooperative, Inc. Richmond Va.) containing solely grain products, and (3) Soy Best (Grain States Soya, Inc., West Point, Nebr.) containing high bypass soybean meal.

Feeds were first ground into powder using a food processor; then the meat meal was added to feed samples on a weight basis to produce 50, 25, 5, and 1% of pork, beef, sheep, horse, deer, chicken, turkey, or catfish in each of the three different feed matrixes. The adulterated samples were mixed with 1:6 (w/v) of 0.5M NaCl and autoclaved at 21° C. for 20 min. The samples were homogenized using a Polytron homogenizer and centrifuged at 15,000×g for 30 min. The supernatant was filtered through a Whatman No. 1 filter paper and the filtrates were used for ELISA analysis.

Results and Discussion

Indirect ELISAs for the Detection of Muscle Tissues in Feed Stuffs

The feasibility of using these MAbs in indirect ELISAs for the detection of rendered muscle tissues in feed stuffs was demonstrated by adding the meat meals into feed samples. Three feed samples containing plant, grain and soy proteins were each spiked with known amounts of meat meals and analyzed by these assays. Unadulterated feed samples (A, B and C) yielded consistent baseline readings; indicating no interference between MAbs and plant constituents in the feed samples. Table 2. The detectability of the assay was less than 1% for all the species analyzed.

The mammalian assay (not shown) correctly identified pork, beef, sheep, horse and deer meats. The ruminant assay (using MAb 2A8) specifically detected beef, sheep, and deer meats in all feed samples (Table 2).

TABLE 2

Absorbance readings of indirect ELISA using MAb 2A8 for the detection of various percentage of ruminant muscles in feed samples

|  | P | B | S | H | D | C | T | Fa |
|---|---|---|---|---|---|---|---|---|
| 0% | Feed Sample A (Natural Beef Builder Coarse) without addition of meat meals 13 (3)b | | | | | | | |
| 1%c | 16(2) | 61(6) | 78(4) | 9(6) | 86(3) | 7(6) | 10(7) | 9(3) |
| 5% | 17(2) | 210(18) | 409(19) | 7(4) | 397(17) | 6(4) | 5(3) | 11(2) |
| 25% | 18(3) | 542(20) | 806(17) | 12(7) | 797(21) | 5(4) | 7(3) | 10(6) |
| 50% | 14(3) | 608(17) | 946(55) | 6(4) | 930(25) | 8(3) | 10(6) | 8(3) |
| 0% | Feed Sample B (Chicken Scratch Feed) without addition of meat meals 13 (4) | | | | | | | |
| 1% | 5(5) | 16(4) | 29(9) | 14(8) | 30(8) | 6(4) | 6(4) | 5(3) |
| 5% | 6(6) | 49(10) | 107(11) | 16(6) | 109(17) | 6(4) | 5(4) | 7(3) |
| 25% | 8(6) | 222(24) | 459(43) | 15(8) | 506(40) | 18(9) | 10(2) | 12(6) |
| 50% | 18(8) | 392(25) | 716(48) | 12(6) | 822(16) | 20(8) | 17(4) | 19(9) |
| 0% | Feed Sample C (Soy Best) without addition of meat meals 16 (4) | | | | | | | |
| 1% | 9(2) | 63(4) | 102(13) | 14(1) | 160(11) | 13(5) | 15(2) | 14(2) |
| 5% | 7(1) | 159(2) | 283(6) | 13(5) | 352(19) | 15(1) | 16(2) | 8(1) |
| 25% | 16(6) | 253(10) | 460(18) | 11(2) | 600(7) | 23(3) | 21(3) | 8(4) |
| 50% | 20(2) | 348(19) | 538(17) | 16(5) | 605(45) | 22(2) | 23(2) | 8(5) | a Species of meat meals added to the feed samples; P = pork, B = beef, S = sheep, H = horse, D = deer, C = chicken, T = turkey, F = catfish.
b Values represent the mean absorbance at 415 nm × 1000 of three repeat measurements. Values in the parentheses are the standard deviations of the three measurements. The absorbance has been corrected using the substrate reagent as blank.
c Feed samples mixed by weight with various percentage (1, 5, 25, and 50%) of meat meals of individual species.

The detection limit of the mammalian and ruminant assays were between 0.3 and 2%, estimated as for the readings above to be three standard deviations of the unadulterated feed samples. The proportions of muscle tissues in meat meals, meat and bone meals, animal meal, and other compound feed stuffs may vary in a wide range. The indirect ELISA assays may not sensitive enough in some circumstances. It is expected that the assay sensitivity could be greatly enhanced (such as 0.1% or less), if sandwich ELISA assays which utilize a pair of these MAbs as specific capture (such as an "all species" MAb—for instance, 2G3).

The ELISA method currently used in the UK detects most of the mammalian proteins without discrimination between prohibited and allowed proteins (Moncilovic et al. (2000) *J. Food Protection* 63(11):1602-1609. Moreover, the method involves a lengthy procedure utilizing ammonium sulfate precipitation to remove gelatin, which interferes with the measurement, and to concentrate proteins, in order to boost the assay sensitivity, Ansfield (1994) *Food & Agric. Imm.* 6:419-433. The MAb based ELISAs Applicants developed detects specifically muscle TnI without cross-reaction to gelatin, blood/serum proteins and milk proteins (data not shown). The entire analysis, including sample extraction, can be performed in less than 6 h. The sensitivity and specificity of these assays make it easily possible to detect low amounts of muscle tissue in feed samples without any concentration procedure.

EXAMPLE 4

Adulteration of Meat Samples

Materials and Methods

Purification of TnI

Purification of TnI is carried out as described in Example 1, above.

Immunization

Immunization is carried out as described in Example 2, above.

Production of Monoclonal Antibodies

The monoclonal antibodies used in Example 2, above, are used in the present experiment.

ELISA

ELISAs are carried out as described in Example 2, above.

SDS-PAGE and Western Blot

Sodium dodecyl sulfate-polyacrylamide gel electrophoresis (SDS-PAGE) is carried out as described in Example 2, above.

Preparation of Adulteration Standards

Meat meals composed of single species are produced in our laboratory. Ground muscles of beef, pork, sheep, horse, deer, chicken, turkey, and catfish are placed in beakers and covered loosely with aluminum foil. The muscles are autoclaved at 132° C. and 2 bar for 2 h, then the meat slurries are dried on sheets of aluminum foil in a convection oven at 80° C. for 24 h. Dry weights of the final products ranged between 23 and 27% of the original material. Dried meats are crumbled into fine granules with a food processor; then individually packed in sealed plastic bags and stored at 4° C.

Meat adulterated samples are prepared by substituting pure cooked pork with different dried poultry 0, 0.1, 0.5, 1, 5, 10, 20, 30, 40, 50, 60, 80 and 100% (wt/wt) levels. The adulterated samples are mixed with 1:6 (w/v) of 0.5M NaCl and autoclaved at 21° C. for 20 min. The samples are homogenized using a Polytron homogenizer and centrifuged at 15,000×g for 30 min. The supernatant is filtered through a Whatman No. 1 filter paper and the filtrates are used for ELISA analysis.

Indirect ELISA using the undiluted supernatants containing MAbs is employed to quantify the substitution of pork with chicken, turkey or duck in the prepared adulterated meats. MAb 5G8 can detect the presence of chicken meat in pork and/or beef. The absorbance increases as the substitution of poultry meats for pork in the test meat extracts is increased. This MAb can detect 0-100% of poultry meats in a non-poultry meat sample. Zero to 100 percent of either chicken or turkey can be quantitatively detected using this MAb in a double sandwich ELISA with MAb 2G3 as the capture antibody.

CONCLUSION

Purified TnI, not blood serum proteins (serum albumin), are used as antigens to produce MAbs in this study. The blood proteins are used to raise polyclonal antibodies in commercial raw meat species identification kits. Their quantity in a given sample does not necessarily parallel the amount of the corresponding species meat (Jones and Patterson (1988). Recent Developments in Meat Specification. In *Immunoassays for Veterinary and Food Analysis*-1, B. A. Morris, M. N. Clifford and R. Jackman (Ed), p. 121-126. Elsevier Applied Science Publishers, London, England). The amount of serum proteins is affected by the residual blood left in the muscle after slaughter (Warris (1977) *Meat Sci.* 2:155-159). Therefore, the presence of serum proteins does not essentially denote the amount of the corresponding muscle tissue. In contrast to serum proteins, the amount of TnI is proportional to the presence of lean meat. It is suitable to be used for both qualitative and quantitative analysis in meat species identification (Martin et al. (1991) *Meat Sci.* 30:23-31).

Detection of small amounts of substituted meat supplies is a concern of consumers and regulatory agencies. The present assay is adequate to illustrate a quantitative detection over a wide range of mixture levels (0-100%). Development of a sandwich ELISA or the use of an avidin-biotin immunoassay, Klein "Antigen-antibody interactions," *Immunology*, 1990, pp. 294-310, Blackwell Scientific Publications, Oxford, England, would increase the sensitivity of the developed MAbs to quantify poultry adulterant in red meat products.

Poultry may be added into pork product due to the similar light color. The unmarketable trimmings of poultry may also be substituted into other red meats. Poultry requires a minimal internal temperature of 71.1° C. to kill *Salmonella*. (USDA-FSIS (1994) Requirements for the production of poultry breakfast strips, poultry rolls, and certain other poultry products. Animals and Animal Products. Part 381.150, p. 495-496 of Chapter III. Title 9 of the Code of Federal Regulations, Office of the Federal Register, National Archives and Records, Washington, D.C.). If beef or lamb product contaminated with poultry was not fully cooked, it might cause Salmonellosis. Hsieh et al. (1995) reported that 18% and 38% of ground pork and pork sausage samples analyzed were contaminated with poultry using ELISA, respectively. About 31% of ground beef and ground veal samples was also contaminated with poultry (Hsieh et al. (1995) *J. Food Prot.* 58:555-559). A high percentage of adulteration with multiple species was also found in the ground pork and ground beef samples. The developed MAb 5G8 can react with three poultry species. Therefore, this MAb could be used in ELISA to detect the presence of poultry as a group in the cooked red meat products in a single test. It would be highly suitable and economical for an initial rapid screening of meat samples. A convenient field test kit could be developed using these MAbs for meat inspectors.

Procedure A.

Retrieve Myeloma Cells From Liquid Nitrogen 1. retrieve myeloma cells from liquid nitrogen
2. put the vial into a 37-39° C. water bath to thaw the cells
3. add 9 ml of growth media (RPMI-1640, 10% FBS, 1% p/s) drop by drop to resuspend the cells
4. centrifuge at 1,700 rpm for 5 min
5. resuspend cell pallet in 5 ml of growth media
6. perform the cell count
7. centrifuge at 1,700 rpm for 5 min
8. resuspend the cells in 5 ml of growth media
9. transfer the cells to the petri dish Procedure B.

Procedure of Freezing Hybridoma Cells

1. Scrape cells from the petri dish
2. centrifuge at 1700 rpm for five minutes to get cell pallet
3. resuspend cell pallet with 500 µl of CGM
4. Add 500 µl of freeze media containing six parts of FBS, two parts of CGM and two parts of dimethyl sulfoxide (DMSO) drop by drop
5. Cell suspension was transferred to a cryogenic vial and stored in liquid nitrogen.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of a distinct type or species of meat from at least one animal species used for human or animal consumption in a sample, said method comprising:
   a) contacting said sample with a species-specific antibody generated from isolated skeletal non-human troponin I (TnI) as an antigen wherein said antibody is monoclonal antibody 1F9 (ATCC Accession No. PTA-8208) or 2G3 (ATCC Accession No. PTA-3782), and wherein said antibody is directly or indirectly conjugated to a label; and
   b) determining whether said antibody binds to non-human troponin I in said sample; wherein binding of said antibody to non-human troponin I in said sample is indicative of the presence of a distinct type or species of meat from at least one animal species used for human or animal consumption in said sample, wherein said distinct type or species of meat is pork, beef, lamb, horse, deer, chicken, turkey, duck, goose, ostrich, or catfish meat.

2. A method for detecting the presence of a distinct type or species of meat from at least one animal species used for human or animal consumption in a sample, said method comprising:
   a) contacting said sample with a species-specific antibody generated from isolated skeletal non-human troponin I (TnI) as an antigen wherein said antibody is monoclonal antibody 8A12 (ATCC Accession No. PTA- 8209), and wherein said antibody is directly or indirectly conjugated to a label; and
  b) determining whether said antibody binds to non-human troponin I in said sample; wherein binding of said antibody to non-human troponin I in said sample is indicative of the presence of a distinct type or species of meat from at least one animal species used for human or animal consumption in said sample, wherein said distinct type or species of meat is pork, bovine, sheep, horse, or deer meat.

3. A method for detecting the presence of a distinct type or species of meat from at least one animal species used for human or animal consumption in a sample, said method comprising:
  a) contacting said sample with a species-specific antibody generated from isolated skeletal non-human troponin I (TnI) as an antigen wherein said antibody is monoclonal antibody 2A8 (ATCC Accession No. PTA-3783), and wherein said antibody is directly or indirectly conjugated to a label; and
  b) determining whether said antibody binds to non-human troponin I in said sample; wherein binding of said antibody to non-human troponin I in said sample is indicative of the presence of a distinct type or species of meat from at least one animal species used for human or animal consumption in said sample, wherein said distinct type or species of meat is bovine, sheep, or deer meat.

4. A method for identifying meat adulteration in an animal feed product, said method comprising:
  a) contacting said sample with a species-specific antibody generated from isolated skeletal non-human troponin I (TnI) as an antigen wherein said antibody is monoclonal antibody 1F9 (ATCC Accession No. PTA-8208) or 2G3 (ATCC Accession No. PTA-3782), and wherein said antibody is directly or indirectly conjugated to a label; and
  b) determining whether said antibody binds to non-human troponin I in said sample; wherein binding of said antibody to non-human troponin I in said sample is indicative of the presence of a distinct type or species of meat from at least one animal species used for human or animal consumption in said sample, wherein said distinct type or species of meat is pork, beef, lamb, horse, deer, chicken, turkey, duck, goose, ostrich, or catfish meat, and wherein the presence of said distinct type or species of meat in said sample is indicative of meat adulteration in said animal feed product.

5. A method for identifying meat adulteration in an animal feed product, said method comprising:
  a) contacting said sample with a species-specific antibody generated from isolated skeletal non-human troponin I (TnI) as an antigen wherein said antibody is monoclonal antibody 8A12 (ATCC Accession No. PTA-8209), and wherein said antibody is directly or indirectly conjugated to a label; and
  b) determining whether said antibody binds to non-human troponin I in said sample;
  wherein binding of said antibody to non-human troponin I in said sample is indicative of the presence of a distinct type or species of meat from at least one animal species used for human or animal consumption in said sample, wherein said distinct type or species of meat is pork, bovine, sheep, horse, or deer meat, and wherein the presence of said distinct type or species of meat in said sample is indicative of meat adulteration in said animal feed product.

6. A method for identifying meat adulteration in an animal feed product, said method comprising:
  a) contacting said sample with a species-specific antibody generated from isolated skeletal non-human troponin I (TnI) as an antigen wherein said antibody is monoclonal antibody 2A8 (ATCC Accession No. PTA-3783), and wherein said antibody is directly or indirectly conjugated to a label; and
  b) determining whether said antibody binds to non-human troponin I in said sample;
  wherein binding of said antibody to non-human troponin I in said sample is indicative of the presence of a distinct type or species of meat from at least one animal species used for human or animal consumption in said sample, wherein said distinct type or species of meat is bovine, sheep, or deer meat, and wherein the presence of said distinct type or species of meat in said sample is indicative of meat adulteration in said animal feed product.

7. A method for identifying meat adulteration in an animal feed product, said method comprising:
  a) combining a feed sample obtained from said animal feed product suspected of containing rendered muscle tissue with a species-specific antibody generated from isolated skeletal non-human troponin I (TnI) as an antigen for a time and under conditions sufficient to form a complex between the antibody and the troponin I molecule, wherein said antibody is monoclonal antibody 1F9 (ATCC Accession No. PTA-8208) or 2G3 (ATCC Accession No. PTA-3782), and wherein said antibody is directly or indirectly conjugated to a label; and
  b) detecting the complex either directly or indirectly as a measure of the presence of a distinct type or species of meat from at least one animal species used for human or animal consumption in said feed sample;
  wherein said distinct type or species of meat is pork, beef, lamb, horse, deer, chicken, turkey, duck, goose, ostrich, or catfish meat, and wherein detecting said complex in said feed sample is indicative of meat adulteration in said animal feed product.

8. A method for identifying meat adulteration in an animal feed product, said method comprising:
  a) combining a feed sample obtained from said animal feed product suspected of containing rendered muscle tissue with a species-specific antibody generated from isolated skeletal non-human troponin I (TnI) as an antigen for a time and under conditions sufficient to form a complex between the antibody and the troponin I molecule, wherein said antibody is monoclonal antibody 8A12 (ATCC Accession No. PTA-8209), and wherein said antibody is directly or indirectly conjugated to a label; and
  b) detecting the complex either directly or indirectly as a measure of the presence of a distinct type or species of meat from at least one animal species used for human or animal consumption in said feed sample;
  wherein said distinct type or species of meat is pork, bovine, sheep, horse, or deer meat, and wherein detecting said complex in said feed sample is indicative of meat adulteration in said animal feed product.

9. A method for identifying meat adulteration in an animal feed product, said method comprising:
  a) combining a feed sample obtained from said animal feed product suspected of containing rendered muscle tissue with a species-specific antibody generated from isolated skeletal non-human troponin I (TnI) as an antigen for a time and under conditions sufficient to form a complex between the antibody and the troponin I molecule, wherein said antibody is monoclonal antibody 2A8 (ATCC Accession No. PTA-3783), and wherein said antibody is directly or indirectly conjugated to a label; and b) detecting the complex either directly or indirectly as a measure of the presence of a distinct type or species of meat from at least one animal species used for human or animal consumption in said feed sample;

wherein said distinct type or species of meat is bovine, sheep, or deer meat, and wherein detecting said complex in said feed sample is indicative of meat adulteration in said animal feed product.

* * * * *